United States Patent [19]
Muzilla et al.

[11] Patent Number: 5,908,391
[45] Date of Patent: Jun. 1, 1999

[54] METHOD AND APPARATUS FOR ENHANCING RESOLUTION AND SENSITIVITY IN COLOR FLOW ULTRASOUND IMAGING USING MULTIPLE TRANSMIT FOCAL ZONES

[75] Inventors: David John Muzilla, Mukwonago; Anne Lindsay Hall, New Berlin; Mir Said Seyed-Bolorforosh, Brookfield; Michael J. Washburn, New Berlin; David D. Becker, Milwaukee; Doralie Martinez, Milwaukee; Xiao-Liang Xu, Brookfield, all of Wis.

[73] Assignee: General Electric Company, Milwaukee, Wis.

[21] Appl. No.: 08/852,700
[22] Filed: May 7, 1997
[51] Int. Cl.$^6$ .................................................. A61B 8/00
[52] U.S. Cl. ......................... 600/454; 600/455; 600/457
[58] Field of Search ................................... 600/447, 454, 600/453, 455; 367/7; 73/625

[56] References Cited

U.S. PATENT DOCUMENTS

| | | | |
|---|---|---|---|
| 5,119,342 | 6/1992 | Harrison, Jr. et al. | 367/7 |
| 5,301,674 | 4/1994 | Erikson et al. | 600/447 |
| 5,379,642 | 1/1995 | Reckwerdt et al. | 73/625 |

*Primary Examiner*—Francis J. Jaworski
*Assistant Examiner*—Ali M. Imam
*Attorney, Agent, or Firm*—Dennis M. Flaherty; Christian G. Cabou; Phyllis Y. Price

[57] ABSTRACT

A method and an apparatus for increasing the spatial resolution and sensitivity of a color flow image while maintaining a desired acoustic frame rate. The ultrasound energy is concentrated at a more narrowly defined focal region, which allows for increased flow sensitivity and vessel filling. Better flow uniformity across the color region of interest is also achieved. The method uses multiple transmit focal zones, and transmit and receive apertures having low f-numbers. Using multiple focal zones with low f-numbers allows for tight focusing over a larger depth-of-field. Unique waveforms and unique gain curves are used for each focal zone. Each focal zone is fired on a separate acoustic frame. An adaptive frame averaging algorithm is used to blend together the in-focus data from each of these acoustic frames before the data is displayed.

23 Claims, 5 Drawing Sheets

ORIGINAL VECTOR SET

DECIMATED VECTOR SET

NON-UNIFORM VECTOR DENSITY LATERALLY ACROSS THE IMAGE

METHOD AND APPARATUS FOR ENHANCING RESOLUTION AND SENSITIVITY IN COLOR FLOW ULTRASOUND IMAGING USING MULTIPLE TRANSMIT FOCAL ZONES

FIELD OF THE INVENTION

This invention generally relates to ultrasound imaging of the human anatomy for the purpose of medical diagnosis. In particular, the invention relates to a method and an apparatus for imaging of moving fluid or tissue in the human body by detecting Doppler shifting of ultrasonic echoes reflected from the moving fluid or tissue.

BACKGROUND OF THE INVENTION

Conventional ultrasound scanners create two-dimensional B-mode images of tissue in which the brightness of a pixel is based on the intensity of the echo return. In color flow imaging, the flow of blood or movement of tissue can be imaged. Measurement of blood flow in the heart and vessels using the Doppler effect is well known. The frequency shift of backscattered ultrasound waves may be used to measure the velocity of the backscatterers from tissue or blood. The change or shift in backscattered frequency increases when blood flows toward the transducer and decreases when blood flows away from the transducer. The Doppler shift may be displayed using different colors to represent speed and direction of flow. The color flow velocity mode displays hundreds of adjacent sample volumes simultaneously, all color-coded to represent each sample volume's velocity. Power Doppler imaging (PDI) is a color flow mode in which the amplitude of the flow signal, rather than the velocity, is displayed. The color flow image may be superimposed on the B-mode image.

The present invention is incorporated in an ultra-sound imaging system consisting of four main subsystems: a beamformer 2 (see FIG. 1), processors 4 (including a separate processor for each different mode), a scan converter/display controller 6 and a kernel 8. System control is centered in the kernel 8, which accepts operator inputs through an operator interface 10 and in turn controls the various subsystems. The master controller 12 performs system level control functions. It accepts inputs from the operator via the operator interface 10 as well as system status changes (e.g., mode changes) and makes appropriate system changes either directly or via the scan controller. The system control bus 14 provides the interface from the master controller to the subsystems. The scan control sequencer 16 provides real-time (acoustic vector rate) control inputs to the beamformer 2, system timing generator 24, processors 4 and scan converter 6. The scan control sequencer 16 is programmed by the host with the vector sequences and synchronization options for acoustic frame acquisitions. Thus, the scan control sequencer controls the beam distribution and the beam density. The scan converter broadcasts the beam parameters defined by the host to the subsystems via scan control bus 18.

The main data path begins with the digitized RF inputs to the beamformer from the transducer. Referring to FIG. 2, a conventional ultrasound imaging system includes a transducer array 36 comprised of a plurality of separately driven transducer elements 38, each of which produces a burst of ultrasonic energy when energized by a pulsed waveform produced by a transmitter (not shown). The ultrasonic energy reflected back to transducer array 36 from the object under study is converted to an electrical signal by each receiving transducer element 38 and applied separately to the beamformer 2.

The echo signals produced by each burst of ultrasonic energy reflect from objects located at successive ranges along the ultrasonic beam. The echo signals are sensed separately by each transducer element 38 and the magnitude of the echo signal at a particular point in time represents the amount of reflection occurring at a specific range. Due to the differences in the propagation paths between an ultrasound-scattering sample volume and each transducer element 38, however, these echo signals will not be detected simultaneously and their amplitudes will not be equal. Beamformer 2 amplifies the separate echo signals, imparts the proper time delay to each, and sums them to provide a single echo signal which accurately indicates the total ultrasonic energy reflected from the sample volume. Each beamformer channel 40 receives the echo signal from a respective transducer element 38.

To simultaneously sum the electrical signals produced by the echoes impinging on each transducer element 38, time delays are introduced into each separate beamformer channel 40 by a beamformer controller 42. The beam time delays for reception are the same delays as the transmission delays. However, the time delay of each beamformer channel is continuously changing during reception of the echo to provide dynamic focusing of the received beam at the range from which the echo signal emanates. The beamformer channels also have circuitry (not shown) for apodizing and filtering the received pulses.

The signals entering the summer 44 are delayed so that they are summed with delayed signals from each of the other beamformer channels 40. The summed signals indicate the magnitude and phase of the echo signal reflected from a sample volume located along the steered beam. A signal processor or detector 4 converts the received signal to display data.

The beamformer outputs two summed digital baseband receive beams. The baseband data is input to B-mode processor 4A and color flow processor 4B, where it is processed according to the acquisition mode and output as processed acoustic vector (beam) data to the scan converter/display processor 6. The scan converter/display processor 6 accepts the processed acoustic data and outputs the video display signals for the image in a raster scan format to a color monitor 22.

The B-mode processor converts the baseband data from the beamformer into a log-compressed version of the signal envelope. The B function images the time-varying amplitude of the envelope of the signal as a grey scale using an 8-bit output for each pixel. The envelope of a baseband signal is the magnitude of the vector which the baseband data represent.

The frequency of sound waves reflecting from the inside of blood vessels, heart cavities, etc. is shifted in proportion to the velocity of the blood cells: positively shifted for cells moving towards the transducer and negatively for those moving away. The color flow (CF) processor is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The structure and operation of a color flow processor are disclosed in U.S. Pat. No. 5,524,629, the contents of which are incorporated by reference herein.

The color flow processor produces velocity (8 bits), variance (turbulence) (4 bits) and power (8 bits) signals. The operator selects whether the velocity and variance or the power are output to the scan converter. The output signal is input to a chrominance control lookup table which resides in the video processor 22. Each address in the lookup table stores 24 bits. For each pixel in the image to be produced, 8 bits control the intensity of red, 8 bits control the intensity of green and 8 bits control the intensity of blue. These bit patterns are preselected such that as the flow velocity changes in direction or magnitude, the color of the pixel at each location is changed. For example, flow toward the transducer is typically indicated as red and flow away from the transducer is typically indicated as blue. The faster the flow, the brighter the color.

In conventional ultrasound imaging systems, the array of ultrasonic transducers transmit an ultrasound beam and then receive the reflected beam from the object being studied. The array typically has a multiplicity of transducers arranged in a line and driven with separate voltages. By selecting the time delay (or phase) and amplitude of the applied voltages, the individual transducers can be controlled to produce ultrasonic waves which combine to form a net ultrasonic wave that travels along a preferred beam direction and is focused at a selected range along the beam. Multiple firings may be used to acquire data representing the desired anatomical information along a multiplicity of scan lines. The beamforming parameters of each of the firings may be varied to provide a change in the position of focus or otherwise change the spatial position of the received data. By changing the time delay and amplitude of the applied voltages, the beam with its focal point can be moved in a plane to scan the object.

The same principles apply when the transducer is employed to receive the reflected sound (receiver mode). The voltages produced at the receiving transducers are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer.

Such scanning comprises a series of measurements in which the steered ultrasonic wave is transmitted, the system switches to receive mode after a short time interval, and the reflected ultrasonic wave is received and stored. Typically, transmission and reception are steered in the same direction during each measurement to acquire data from a series of points along a scan line. The receiver is dynamically focused at a succession of ranges or depths along the scan line as the reflected ultrasonic waves are received.

In an ultrasound imaging system, the beam spacing for an optimum image is determined by the beam width or lateral point spread function. The lateral point spread function is determined by the product of the wavelength and the f-number. The wavelength is in turn a function of the transmit waveform center frequency and the receiver demodulation frequency. The f-number equals the focal depth divided by the aperture.

The number of beams fired is determined by the spatial sampling requirements and the desired frame rate. Frame rate is inversely proportional to the time taken to transmit and receive all the beams required to form a complete frame of data. High frame rates are required to minimize the possible motion-induced errors in the image. In order to maintain a high frame rate the number of beams is kept to the minimum which would satisfy the Nyquist spatial sampling requirement. When fewer beams are fired than minimum spatial sampling requirements, spatial aliasing occurs. At the optimum spatial sampling the highest resolution is obtained together with the highest frame rate.

SUMMARY OF THE INVENTION

The present invention is a method and an apparatus for increasing the spatial resolution and sensitivity of a color flow image while maintaining a desired acoustic frame rate. In accordance with the invention, the ultrasound energy is concentrated at a more narrowly defined focal region, which allows for increased flow sensitivity and vessel filling. Better flow uniformity across the color region of interest (ROI) is also achieved.

The method of the invention employs a number of techniques, including the use of multiple transmit focal zones and transmit and receive apertures having low f-numbers, i.e., 1.0 to 3.0. Using multiple transmit focal zones with low f-numbers allows for tight focusing over a larger depth-of-field. Furthermore, unique waveforms and unique gain curves are used for each transmit focal zone. Each transmit focal zone is fired on a separate acoustic frame. An adaptive frame averaging algorithm is used to blend together the in-focus data from each of these acoustic frames as the data is displayed. The advantage of this method is that there is no further reduction of real frame rate, since no additional firings are needed over the traditional single-focus color mode.

The system of the present invention stores a multiplicity of so-called "multi-frequency set-ups". Each multi-frequency set-up is a unique beamforming and waveform set-up. Each of these set-ups uses different waveforms with different numbers of transmit cycles (i.e., burst lengths), different f-numbers, etc. These multi-frequency set-ups are defined in the transducer probe files by so-called "fast" and "slow" beamforming parameters. These parameters define the waveform being transmitted, how the aperture is being used (f-numbers, apodization, etc.), how the signal is demodulated on receive, the focal zone positions, and several other parameters. A slow/fast beamforming pair generally defines a multi-frequency set-up.

The fast beamforming parameters are those parameters which can be changed without causing a significant transition delay when the user changes applications or multi-frequency set-ups. The slow beamforming parameters are those parameters which require a new beamforming set-up to be loaded into system memory, causing a delay of a few seconds when the user changes applications or multi-frequency set-ups which use a different slow beamforming set-up.

DETAILED DESCRIPTION OF THE PREFERRED EMBODIMENTS

Figure 3:
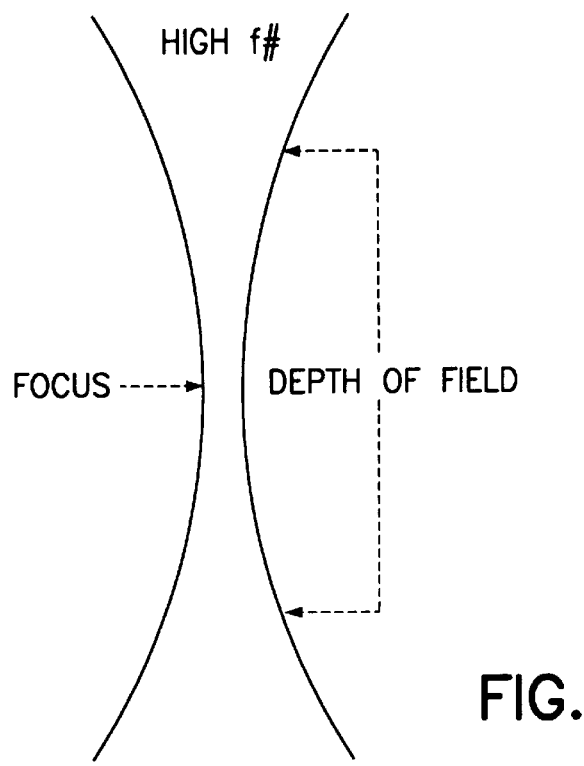
FIG. 3 is a schematic depicting the acoustic beam profile which results when the ultrasound transducer array has an aperture with a relatively high f-number.
Figure 4:
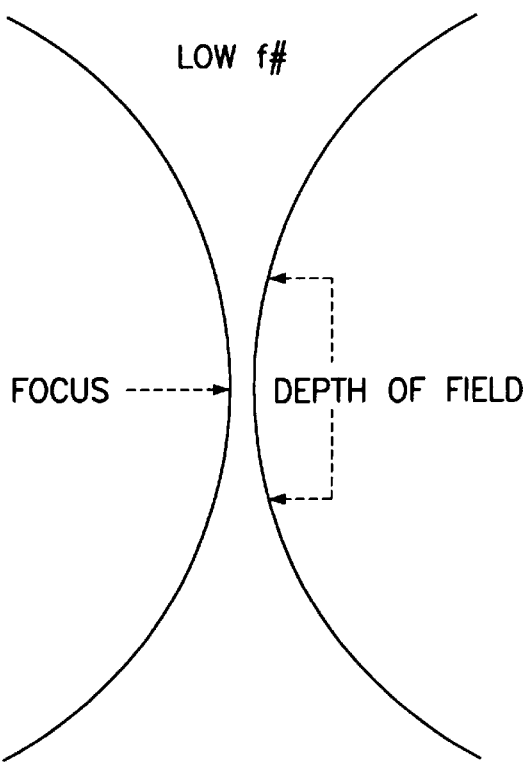
FIG. 4 is a schematic depicting the acoustic beam profile which results when the ultrasound transducer array has an aperture with a relatively low f-number.

In accordance with one aspect of the present invention, low transmit and receive f-numbers (i.e., wide apertures) are used to enhance spatial resolution. The effect on the acoustic beam profile of using low f-number apertures is depicted in FIGS. 3 and 4. FIG. 3 shows the result of using a higher f-number (less aperture). Lateral focusing is not very sharp at the focal point even though the depth-of-field is fairly large in the range dimension. The beam shown in FIG. 4 is the result of using a lower f-number (more aperture). Lateral focusing is tighter at the focal point and the depth-of-field is narrower. In accordance with the preferred embodiments of the invention, the range of f-numbers is from 1.0 to 3.0.

Figure 5:
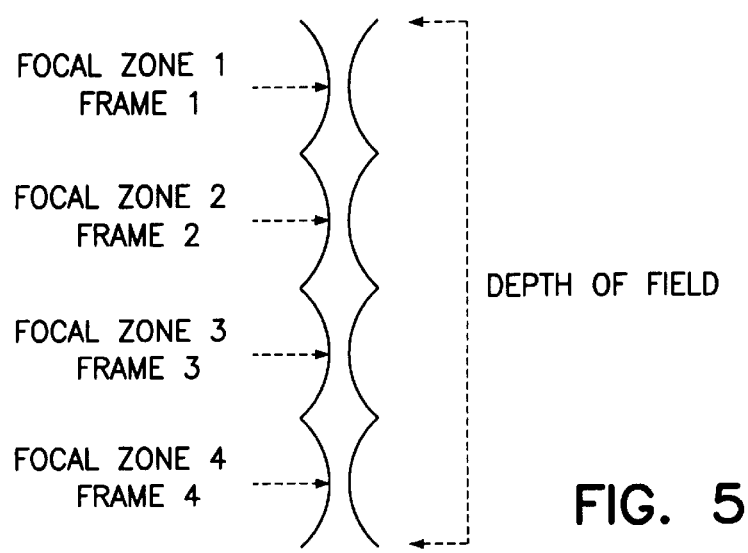
FIG. 5 is a schematic depicting the acoustic beam profile which results when multiple transmit focal zones are used in accordance with the present invention.

In accordance with a further feature of the present invention, multiple transmit focal zones are used. Using multiple focal zones with low f-numbers solves the depth-of-field problem, allowing for tight focusing over a larger depth-of-field as shown in FIG. 5. Transmit focal zone spacing is proportional to the f-number times the wavelength.

In addition, unique waveforms can be used for each focal zone. In the near-field, the transmit waveforms have relatively short burst lengths. The use of shorter-burstlength waveforms results in better axial resolution while trading off sensitivity (less energy in the waveform), which can be compensated for using more aperture in the near-field. Longer-burstlength waveforms are often needed in the far field to achieve the required penetration. In accordance with a further aspect of the invention, the transmit waveforms can vary from focal zone to focal zone. Using a lower-frequency waveform results in more penetration at depth and using a higher-frequency waveform results in better near-field resolution. The preferred range for the demodulation frequency is 1.25 to 8 MHz, depending on the probe, and the preferred number of transmit cycles (i.e., the burst length) for each focal zone is 2 to 8 cycles, depending on the transmit focal depth, center frequency and desired axial resolution. For example, in accordance with one high-resolution beamforming setup, the demodulation frequency is 5 MHz for all focal zones; the number of transmit cycles is 3 for the first 10 focal zone positions (e.g., covering from 0.4 to 3.1 cm); and the number of transmit cycles is 4 for the 11th and 12th focal zone positions (e.g., at 3.4 and 3.7 cm, respectively).

In accordance with yet another aspect of the invention, unique gain curves are used for each focal zone. The term "gain curve" as used herein refers to the manner in which the receiver gain of the system changes with depth. At deeper depths more gain is needed than at shallower depths because attenuation of the acoustic signal is greater at deeper depths. To create a relatively uniform image over depth (uniform in gain), more gain typically needs to be applied at deeper depths. However, in accordance with the invention, most of the energy of the transmitted signal appears at or near the transmit focal zone. Gain matching is done using a unique gain curve for each focal zone. The gain is adjusted so the signal is somewhat higher at the focal zone and less away from the focal zone. In this way, the frame averaging algorithm captures the higher infocus signal and minimizes out-of-focus contributions from the "away" focal zones. The gain curves are a set of numbers in a file for each focal zone, which numbers represent the gain applied to the signal in that stage of the processing. These gain curves are applied on the equalization board, which is part of the beamformer.

The firing of multiple focal zones, in accordance with the invention, presents a challenge for the already frame-rate-limited color imaging mode, since complete packets need to be fired for each focal zone. This challenge is overcome by firing each focal zone on a separate acoustic frame. Thus, the focal zone position is changing from frame to frame.

When scanning in the color flow mode, a two-dimensional image is created by firing one vertical vector after another from left to right to build up a single two-dimensional set of pixel data which will form the image. This set of vertical data vectors is known as an acoustic frame of color flow data. When scanning in the color flow mode, as each acoustic frame of color flow data is acquired, it is processed further while the next acoustic frame of data is being acquired. In accordance with the concept of the present invention, each acoustic frame has one transmit focal zone position for its vectors which can be different from the focal zone position of the previous and subsequent acoustic frames. An adaptive frame averaging algorithm is used to blend together the in-focus data from each of these acoustic frames in preparation for display. In accordance with the preferred embodiment, the focal zones are combined using a non-linear, data-dependent frame-averaging algorithm. The advantage of this method is that there is no further reduction of real frame rate, since no additional firings are needed over the traditional single-focus color mode. Any given flow signal level in the image would be stronger in amplitude when the focal zone nearest to that flow was transmitted. That same flow would appear weaker in amplitude when the other "away" focal zones fired. The frame averaging algorithm takes advantage of this fact by persisting the stronger, in-focus flow amplitude more than the weaker out-of-focus flow amplitude, creating a resultant displayed image which gives both higher spatial resolution and greater sensitivity. This works well in the velocity mode also since weaker out-of-focus flow, away from the transmit focal zone, tends to drop below the velocity mode amplitude threshold and is not displayed. The strong in-focus flow at and near the transmit focus tends to be above this threshold and therefore the velocity signal gets displayed.

In accordance with the preferred embodiment of the invention, the ultrasound imaging system has a total of 12 transmit focal zone positions available for color flow imaging. These focal zone positions can be defined differently in each slow beamforming set-up. One, two, three, or four contiguous focal zones can be active within the ROI at any one time depending on user selection and default settings. Each focal zone is fired on a different acoustic frame and the frame averaging algorithm is then used to combine successive focal zones together to form images for display. There are also unique gain curves which are defined per focal zone, to match the gain over the depth-of-field.

The invention allows for up to three different multi-frequency set-ups per probe which will be user selectable and can be preset across all the individual applications. There will also be three application groups defined, each of which can have up to three different multi-frequency set-ups. This allows for a possible maximum of nine (3×3) unique beamforming set-ups. Each unique beamforming set-up consists of a unique set of fast and slow beamforming parameters. The key fast beamforming parameters include at least the following: (1) demodulation frequency by focal zone; (2) waveform by focal zone; (3) number of transmit cycles by focal zone; (4) the frequency offset applied to the incoming received signal before being shifted to baseband (to line up the center frequency of the received signal with the low-pass equalization filter to maximize the signal-to-noise ratio); (5) ringdown time; and (6) maximum amount of temporal interpolation allowed. The key slow beamforming parameters include: (1) focal zone positions; (2) minimum transmit f-number; and (3) minimum receive f-number.

In addition, unique equalization filters can be defined for each multi-frequency option for each focal zone, separately for velocity and power Doppler imaging modes. This allows for optimal front-end matched filtering per focal zone to maximize received signal-to-noise.

The more the acoustic frame rate can be increased, the better the temporal characteristics of the flow will look to the user and the easier it will be for the frame averaging algorithm to handle combining the acoustic frames. Due to the fact that different focal zones will be fired on different acoustic frames, any given focal zone will only be updated every n acoustic frames, where n is the number of active transmit focal zones in the ROI, i.e., 1, 2, 3 or 4. If the frame averaging and gain matching are not handled correctly for the real frame rate and number of focal zones, problems such as image flicker may occur. Also, out-of-focus flow may be unnecessarily displayed.

The frame averaging algorithm allows for the display of the in-focus flow and minimizes frame-to-frame image flicker as a function of real frame rate and number of active focal zones. The frame averaging is performed by a one-tap IIR filter, which determines the level of persistence based on the color data between the previous and the current frames. Due to the nature of the color flow imaging of the present invention, which requires multiple focal zones, the color flow data, corresponding to each focal zone, must be held valid while all other focal zones are being fired. Another function which must be provided by the frame averaging is to give a higher priority to the strongest color signal between successive frames. This would indirectly provide a function which would splice the data and join them together in an adaptive manner. At any frame, the strongest signal comes from the regions close to the transmit focal point. This is the data that must be displayed on the monitor while all the other transmit focal zones are being fired. The duration for which the data is held valid depends on the number of active transmit focal zones, the signal intensity and the user selection of persistence level. The frame averaging must meet all of these requirements.

In accordance with the preferred embodiment of the present invention, the X-Y display memory (not shown) in the scan converter 6 has a filter comprising a lookup table of output values which represent frame-averaged data. This frame-averaged data is generated off-line using the algorithm depicted in FIG. 6. The outputs $Y_n$ computed in accordance with the algorithm are stored as part of the look-up table.

The frame-averaging circuit of the present invention comprises a random access memory (RAM) located on the X-Y display memory board. The RAM has two inputs and an output. The look-up table is stored in the RAM. One input receives the current frame of non-frame-averaged pixel data. The other input receives the previous frame of frame-averaged pixel data via a time delay device which delays the previous frame data by a time equal to the inverse of the frame rate.

Figure 6:
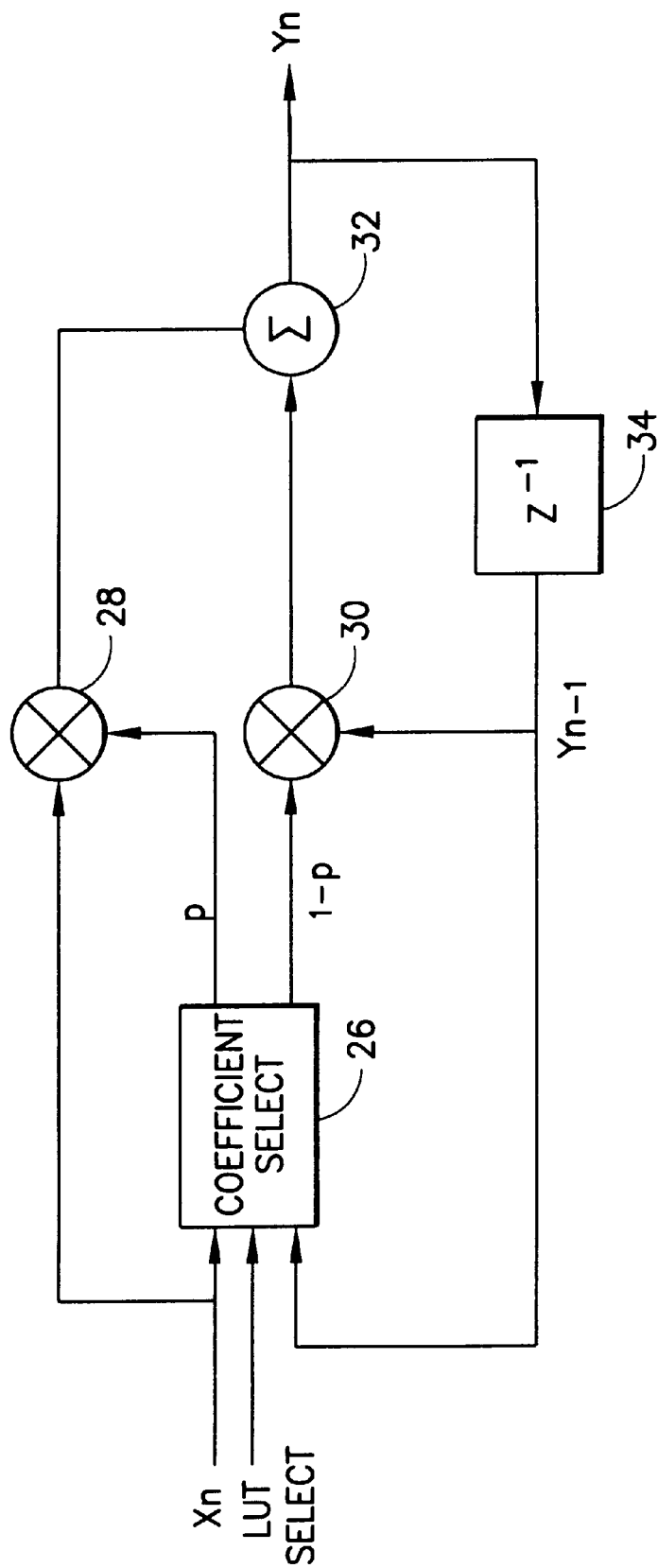
FIG. 6 is a schematic block diagram showing the algorithm for generating the output values to be included in the frame averaging look-up table in accordance with the present invention.

The frame-averaging filtering function is implemented off-line by the algorithm depicted in FIG. 6. The filter outputs are stored on-line in the form of the look-up table. The algorithm comprises a coefficient select step 26 in which persistence coefficients are computed and selected. The coefficient selection is a function of the acoustic frame rate, the number of focal zones and the desired persistence level. These factors are grouped together and indicated in FIG. 6 as an "LUT SELECT" input.

In the algorithm, the selected persistence coefficient p is output to one input of a first multiplier 28. The other input of multiplier 28 represents the unfiltered current frame input $X_n$. Thus the output of multiplier 28 is the product $pX_n$. As a result of the coefficient selection step 26, the value (1−p) is output to one input of a second multiplier 30. The other input of multiplier 30 represents the frame-averaged previous frame output $Y_{n-1}$ from a time delay device 34, which provides a delay equal to the inverse of the frame rate. Thus, the output of multiplier 30 is the product $(1-p)Y_{n-1}$. The outputs of both multipliers are input to a summer 32, which in turn yields the frame-averaged current frame output:

$$Y_n = pX_n + (1-P)Y_{n-1} \tag{1}$$

In accordance with the preferred embodiment of the invention, the RAM chip is loaded with a subset of a multiplicity of look-up tables which are generated off-line and contain the output values $Y_n$. The look-up tables are designed for specific operating parameters and are, as previously indicated, a function of the acoustic frame rate, the number of focal zones and the desired persistence level.

Each look-up table consists of a multiplicity of output values $Y_n$ which were generated off-line by the frame-averaging algorithm of the present invention. In response to the selection of various operating parameters by the system operator, the appropriate look-up table is downloaded into the RAM chip. This look-up table is then addressed by the combined inputs of the unfiltered current frame input $X_n$ and the frame-averaged previous frame output $Y_{n-1}$ to select the outputs $Y_n$ which are the result of the off-line frame-averaging filtering function.

In accordance with the frame-averaging method of the present invention, the output values $Y_n$ are precomputed using persistence coefficients which are a function of the normalized difference $\Delta_{norm}$ between the signal levels of the previous frame and the current frame. This is achieved by taking the absolute difference between the signal levels of the current frame and the previous frame and dividing the result by the arithmetic (or geometric) mean of the two data:

$$\Delta_{norm} = |X_n - Y_{n-1}|/(|X_n + Y_{n-1}|/2) \tag{2}$$

The result of Eq. (2) is used to determine the amount of persistence in the image. The persistence is defined by how much of the data in the previous and current frames are to be used to determine the output signal $Y_n$ (see Eq. (1)), where the persistence coefficient p is either:

$$p = 1 - f(-((\Delta_{norm} - k_1)k_2) + k_4)^{k_3} \tag{3}$$

or $$p = k + f(((\Delta_{norm} - k_1)k_2) + k_4)^{k_3} \tag{4}$$

where f is a nonlinear function, and k, $k_1$, $k_2$, $k_3$ and $k_4$ are constants having values dependent on the number of active transmit focal zones, the acoustic frame rate and persistence level selected by the system operator. The preferred f function is the exponential (exp) function for Eq. (3) and the hyperbolic tangent (tanh) function for Eq. (4). The preferred method for precomputing the frame-averaged output values uses persistence coefficients generated in accordance with Eq. (4) using the tanh function.

An output value $Y_n$ is computed for each possible pair of $X_n$ and $Y_{n-1}$ values for each one of a multiplicity of sets of operating conditions. The output values $Y_n$ are stored as separate look-up tables in system memory, one unique look-up table for each set of operating conditions. The appropriate look-up table is stored in the RAM chip in response to selection of the desired operating conditions, e.g., acoustic frame rate, number of focal zones and persistence level, by the system operator. The pixel data is then frame-averaged in accordance with the filter output values read from the look-up table for as long as the selected operating parameters remain in effect. The input data can be either scan-converted frame data or acoustic line data (non-scan-converted).

Figure 1:
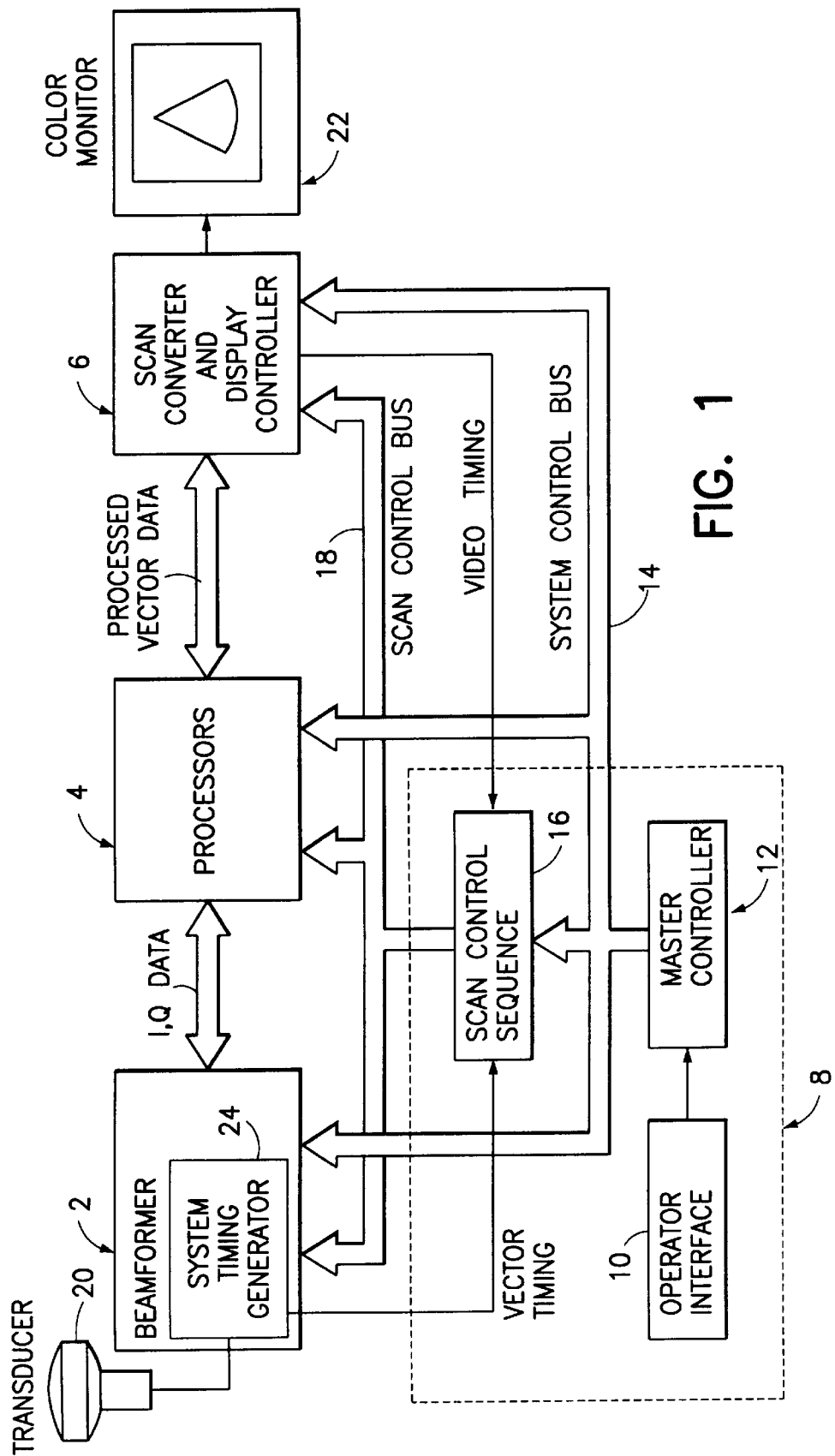
FIG. 1 is a block diagram showing the major functional subsystems within a real-time ultrasound imaging system.
Figure 2:
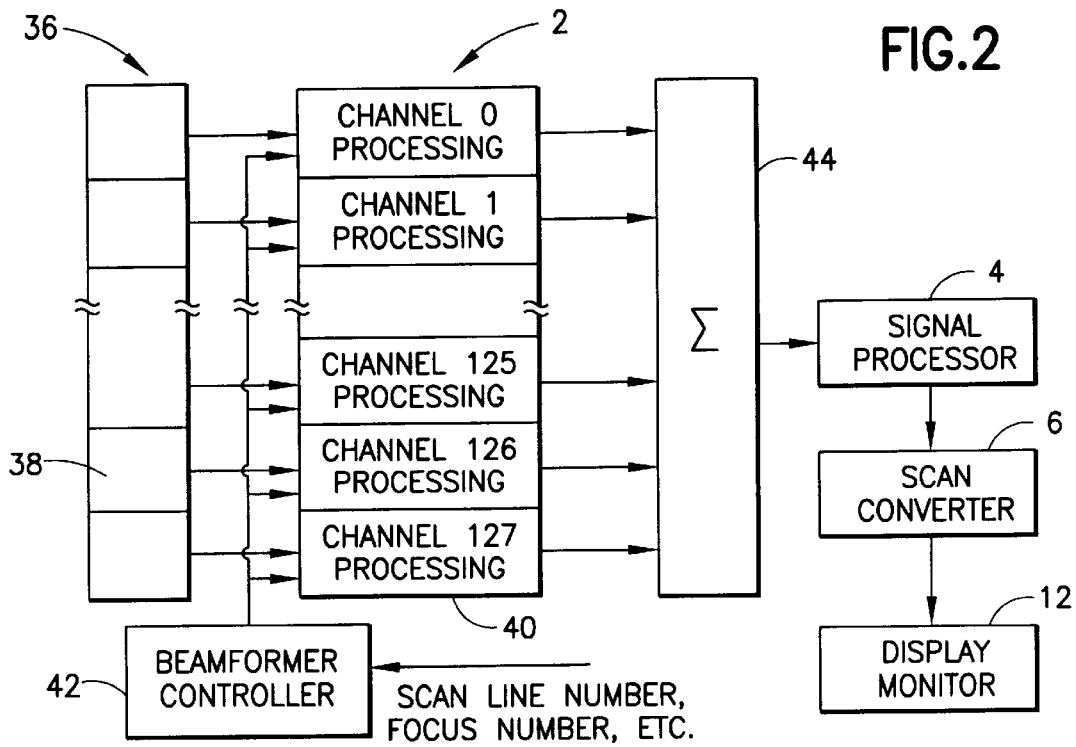
FIG. 2 is a block diagram of a typical 128-channel beamformer in a conventional ultrasound imaging system.
Figure 7A:
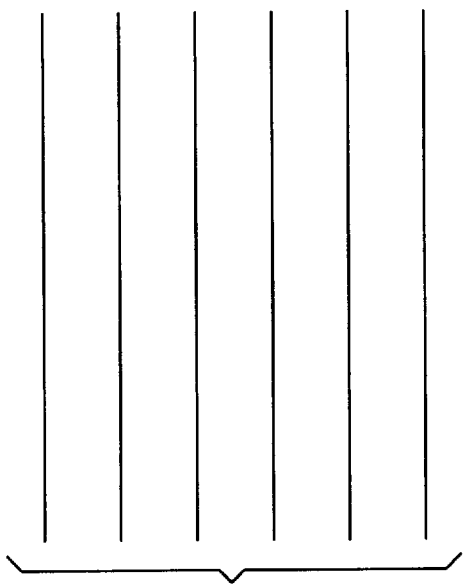
FIGS. 7A and 7B are schematics depicting undecimated and decimated lateral vector distributions, respectively.
Figure 7B:
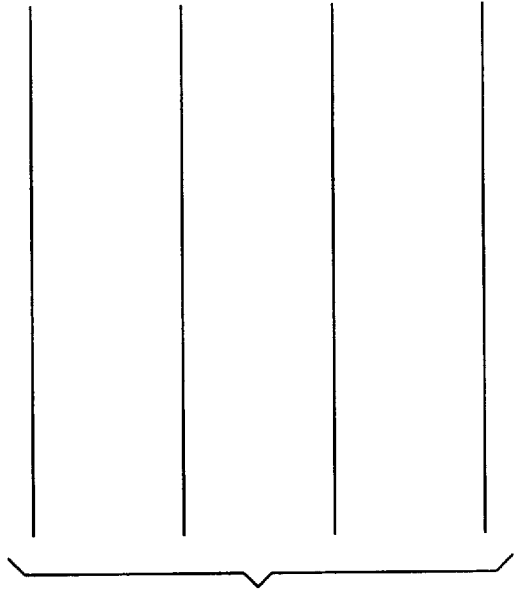
Figure 8:
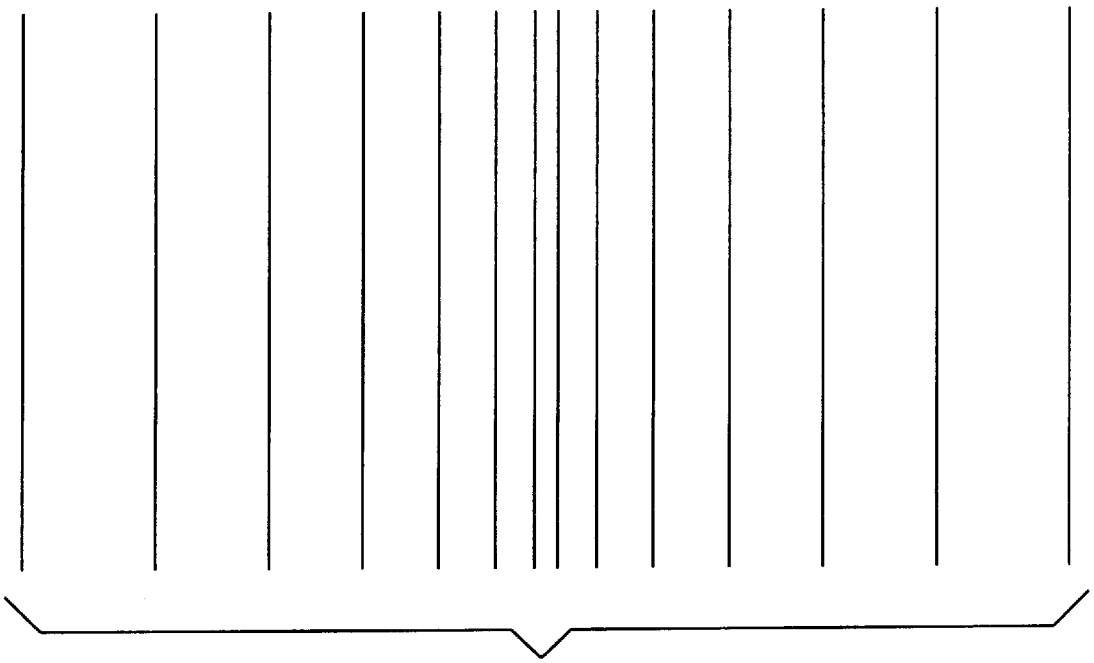
FIG. 8 is a schematic depicting a non-uniform distribution of vectors laterally across the image frame.

In accordance with yet another aspect of the present invention, the vector density can be decimated in order to maintain the desired acoustic frame rate. A maximum of two beamformed vector density sets can be defined for the color flow mode. Referring to FIG. 1, the scan control sequencer 16 is programmed by the host with these vector density sets. To allow for trading off resolution for frame rate, the ability to decimate to a lower vector density from either of the two original vector densities is provided, as shown in FIGS. 7A and 7B. Also, nonuniform distribution of vectors is allowed laterally across the image, as depicted in FIG. 8. Preferably, a parabolic distribution is used, although vector distribution according to the invention is not limited to a parabolic spacing function. Non-uniform vector distribution allows fewer vectors to be used on the sides of the image compared to the center of the image as the aperture gets smaller when imaging towards the edges of the image. This allows the frame rate to be improved while maintaining the high-resolution vector density in the image center where the full aperture can be used.

The foregoing preferred embodiments have been disclosed for the purpose of illustration. Variations and modifications of the concepts of the invention will be readily apparent to those skilled in the arts of ultra-sound imaging. All such variations and modifications are intended to be encompassed by the claims set forth hereinafter

We claim:

1. A method for imaging a medium of moving ultrasound scatterers, comprising the steps of:

transmitting a first set of ultrasound beams toward said medium for producing a first frame of pixel flow data, each of said ultrasound beams of said first set having a first transmit focal zone position;

transmitting a second set of ultrasound beams toward said medium for producing a second frame of pixel flow data, each of said ultrasound beams of said second set having a second transmit focal zone position different than said first transmit focal zone position;

acquiring said first and second frames of pixel flow data in succession, said second frame being acquired after said first frame;

outputting a first current frame of frame-averaged pixel flow data as a function of a frame-averaging algorithm, said second frame of pixel flow data, and a previously outputted frame of frame-averaged pixel flow data, said previously outputted frame having been in turn outputted as function of said frame-averaging algorithm, said first frame of pixel flow data and a next previously outputted frame of frame-averaged pixel flow data; and displaying said first current frame of frame-averaged pixel flow data.

2. The method as defined in claim 1, wherein said pixel flow data comprises flow velocity data.

3. The method as defined in claim 1, wherein said pixel flow data comprises power Doppler data.

4. The method as defined in claim 1, wherein a first gain curve is applied to said first frame of pixel flow data and a second gain curve, different than said first gain curve, is applied to said second frame of pixel flow data.

5. The method as defined in claim 1, wherein an ultrasound beam of said first set has a first burst length and an ultrasound beam of said second set has a second burst length different than said first burst length.

6. The method as defined in claim 1, wherein an ultrasound beam of said first set has a first center frequency and an ultrasound beam of said second set has a second center frequency different than said first center frequency.

7. The method as defined in claim 1, wherein said first and second sets of ultrasound beams are transmitted using a transducer array having an aperture with f-number in the range of 1.0 to 3.0.

8. The method as defined in claim 1, wherein ultrasound echoes are received using a transducer array having an aperture with f-number in the range of 1.0 to 3.0.

9. The method as defined in claim 1, wherein said frame averaging algorithm calculates a persistence coefficient which is a function of the normalized difference between the signal levels of said first and second frames.

10. The method as defined in claim 1, further comprising the steps of:

transmitting a third set of ultrasound beams toward said medium for producing a third frame of pixel flow data, each of said ultrasound beams of said third set having a third transmit focal zone position different than either of said first and second transmit focal zone positions;

acquiring said third frame of pixel flow data after acquisition of said second frame;

outputting a second current frame of frame-averaged pixel flow data as a function of said frame-averaging algorithm, said third frame of pixel flow data, and said first current frame of frame-averaged pixel flow data; and displaying said second current frame of frame-averaged pixel flow data.

11. A system for imaging a medium of moving ultrasound scatterers, comprising:

means for transmitting a first set of ultrasound beams toward said medium for producing a first frame of pixel flow data, each of said ultrasound beams of said first set having a first transmit focal zone position;

means for transmitting a second set of ultrasound beams toward said medium for producing a second frame of pixel flow data, each of said ultrasound beams of said second set having a second transmit focal zone position different than said first transmit focal zone position;

means for acquiring said first and second frames of pixel flow data in succession, said second frame being acquired after said first frame;

filter averaging means for outputting a first current frame of frame-averaged pixel flow data as a function of a frame averaging algorithm, said second frame of pixel flow data, and a previously outputted frame of frame-averaged pixel flow data, said previously outputted frame having been in turn outputted as a function of said frame averaging algorithm, said first frame of pixel flow data and a next previously outputted frame of frame-averaged pixel flow data;

a display monitor; and means for displaying said first current frame of frame-averaged pixel flow data on said display monitor.

12. The system as defined in claim 11, wherein said acquiring means comprise means for computing flow velocity.

13. The system as defined in claim 11, wherein said acquiring means comprise means for computing flow power.

14. The system as defined in claim 11, further comprising means for storing first and second gain curves, said first gain curve being different than said second gain curve, means for applying said first gain curve to said first frame of pixel flow data, and means for applying said second gain curve to said second frame of pixel flow data.

15. The system as defined in claim 11, wherein an ultrasound beam of said first set has a first burst length and an ultrasound beam of said second set has a second burst length different than said first burst length.

16. The system as defined in claim 11, wherein an ultrasound beam of said first set has a first center frequency and an ultrasound beam of said second set has a second center frequency different than said first center frequency.

17. The system as defined in claim 11, further comprising a transducer array having a transmit aperture with f-number in the range of 1.0 to 3.0.

18. The system as defined in claim 11, further comprising a transducer array having a receive aperture with f-number in the range of 1.0 to 3.0.

19. The system as defined in claim 11, wherein said frame averaging algorithm calculates a persistence coefficient which is a function of the normalized difference between the signal levels of said first and second frames.

20. A method for imaging a medium of moving ultrasound scatterers, comprising the steps of:

storing a vector density set;

decimating said vector density set;

transmitting a first set of ultrasound beams toward said medium for producing a first frame of pixel flow data, each of said ultrasound beams of said first set having a first transmit focal zone position and being transmitted in accordance with said decimated vector density set;

transmitting a second set of ultrasound beams toward said medium for producing a second frame of pixel flow data, each of said ultrasound beams of said second set having a second transmit focal zone position different than said first transmit focal zone position and being transmitted in accordance with said decimated vector density set;

acquiring said first and second frames of pixel flow data in succession, said second frame being acquired after said first frame;

outputting a first current frame of frame-averaged pixel flow data as a function of a frame averaging algorithm, said second frame of pixel flow data, and a previously outputted frame of frame-averaged pixel flow data, said previously outputted frame having been in turn outputted as function of said frame averaging algorithm, said first frame of pixel flow data and a next previously outputted frame of frame-averaged pixel flow data; and displaying said first current frame of frame-averaged pixel flow data.

21. A system for imaging ultrasound scatterers, comprising:

an array of ultrasound transducer elements;

a display monitor for displaying an image which is a function of an image signal;

a computer programmed to perform the following steps:

(a) driving elements of said array to transmit a first set of ultrasound beams for producing a first frame of pixel flow data, each of said ultrasound beams of said first set having a first transmit focal zone;

(b) driving elements of said array to transmit a second set of ultrasound beams for producing a second frame of pixel flow data, each of said ultrasound beams of said second set having a second transmit focal zone different than said first transmit focal zone;

(c) acquiring said first and second frames of pixel flow data in succession, said second frame being acquired after said first frame;

(d) outputting a first current frame of frame-averaged pixel flow data as a function of a frame-averaging algorithm, said second frame of pixel flow data, and a previously outputted frame of frame-averaged pixel flow data, said previously outputted frame having in turn been outputted as function of said frame-averaging algorithm, said first frame of pixel flow data and a next previously outputted frame of frame-averaged pixel flow data; and (e) displaying said first current frame of frame-averaged pixel flow data.

22. The system as recited in claim 21, wherein said computer is further programmed to apply a first gain curve to said first frame of pixel flow data and a second gain curve, different than said first gain curve, to said second frame of pixel flow data.

23. The system as recited in claim 21, wherein said computer is further programmed to perform the following steps:

(f) driving elements of said array to transmit a third set of ultrasound beams for producing a third frame of pixel flow data, each of said ultrasound beams of said third set having a third transmit focal zone different than said first and second transmit focal zones;

(g) acquiring said third frame of pixel flow data after said second frame;

(h) outputting a second current frame of frame-averaged pixel flow data as a function of said frame-averaging algorithm, said third frame of pixel flow data, and said first current frame of frame-averaged pixel flow data; and (i) displaying said second current frame of frame-averaged pixel flow data.

* * * * *

UNITED STATES PATENT AND TRADEMARK OFFICE
CERTIFICATE OF CORRECTION

PATENT NO. : 5,908,391
DATED : June 1, 1999
INVENTOR(S) : David J. Muzilla et al.

It is certified that error appears in the above-identified patent and that said Letters Patent is hereby corrected as shown below:

The subscript italic letter "l" (el) should be changed to a subscript number "1" (one) on each of the following occurrences:

in Column 8, at lines 17, 19, 39 and 63, and in equations (1), (2), (3) and (4); and in Column 9, at line 6.

Also, in equation (1) in Column 8, upper-case "P" should be changed to lower-case "p".

Signed and Sealed this

Twelfth Day of October, 1999

Attest:

Q. TODD DICKINSON

*Attesting Officer*  *Acting Commissioner of Patents and Trademarks*